(12) United States Patent
Tsukamoto et al.

(10) Patent No.: US 7,101,642 B2
(45) Date of Patent: Sep. 5, 2006

(54) RECHARGEABLE LITHIUM BATTERY FOR TOLERATING DISCHARGE TO ZERO VOLTS

(75) Inventors: Hisashi Tsukamoto, Saugus, CA (US); Clay Kishiyama, Burbank, CA (US); Mikito Nagata, Valencia, CA (US); Hiroshi Nakahara, Santa Clarita, CA (US); Tiehua Piao, Valencia, CA (US)

(73) Assignee: Quallion LLC, Sylmar, CA (US)

( * ) Notice: Subject to any disclaimer, the term of this patent is extended or adjusted under 35 U.S.C. 154(b) by 454 days.

(21) Appl. No.: 10/262,490

(22) Filed: Sep. 30, 2002

(65) Prior Publication Data

US 2003/0025482 A1    Feb. 6, 2003

Related U.S. Application Data

(60) Continuation-in-part of application No. 10/217,967, filed on Aug. 13, 2002, and a continuation-in-part of application No. PCT/US01/43820, filed on Nov. 19, 2001, and a continuation-in-part of application No. 09/675,287, filed on Sep. 29, 2000, now Pat. No. 6,596,439, and application No. 10/217,967, which is a division of application No. 09/675,287.

(60) Provisional application No. 60/199,895, filed on Apr. 26, 2000.

(51) Int. Cl.
*H01M 4/52* (2006.01)

(52) U.S. Cl. .................. 429/245; 429/231.95; 429/223; 429/231.3

(58) Field of Classification Search ................ 429/245, 429/223, 231.3, 231.95
See application file for complete search history.

(56) References Cited

U.S. PATENT DOCUMENTS

| 4,092,464 A | 5/1978 | Dey et al. |
| 4,935,316 A | 6/1990 | Redey |
| 5,053,297 A | 10/1991 | Yamahira et al. |
| 5,264,201 A * | 11/1993 | Dahn et al. ............... 252/519.1 |
| 5,278,000 A | 1/1994 | Huang et al. |
| 5,411,537 A | 5/1995 | Munshi |
| 5,478,674 A | 12/1995 | Miyasaka |
| 5,500,583 A | 3/1996 | Buckley et al. |
| 5,578,398 A | 11/1996 | Jenkins et al. |
| 5,591,546 A | 1/1997 | Nagaura |
| 5,614,331 A | 3/1997 | Takeuchi |
| 5,631,100 A * | 5/1997 | Yoshino et al. ............... 429/62 |
| 5,783,333 A | 7/1998 | Mayer |
| 5,828,202 A | 10/1998 | Tamai |

(Continued)

FOREIGN PATENT DOCUMENTS

JP    63-314778 A2    12/1988

(Continued)

OTHER PUBLICATIONS

K. Colbow et al., Structure and Electrochemistry of the Spinal Oxides $LiTi_2O_4$ and $Li_{4/3}Ti_{5/3}O_4$. Journal of Power Sources, 1989, pp. 397-402, vol. 26.

(Continued)

*Primary Examiner*—Mark Ruthkosky
(74) *Attorney, Agent, or Firm*—Gavrilovich, Dodd & Lindsey

(57) ABSTRACT

A lithium ion battery particularly configured to be able to discharge to a very low voltage, e.g. zero volts, without causing permanent damage to the battery. More particularly, the battery is configured to define a Zero Volt Crossing Potential (ZCP) which is lower than a Damage Potential Threshold (DPT). A method for using a battery capable of tolerating discharge to zero volts is also disclosed.

24 Claims, 8 Drawing Sheets

U.S. PATENT DOCUMENTS

| | | | |
|---|---|---|---|
| 6,017,654 | A | 1/2000 | Kumta et al. |
| 6,124,062 | A | 9/2000 | Horie et al. |
| 6,159,636 | A * | 12/2000 | Wang et al. .............. 429/223 |
| 6,181,105 | B1 | 1/2001 | Cutolo et al. |
| 6,185,452 | B1 | 2/2001 | Schulman et al. |
| 6,204,634 | B1 | 3/2001 | Zimmerman et al. |
| 6,207,326 | B1 | 3/2001 | Kawakami et al. |
| 6,245,464 | B1 | 6/2001 | Spillman et al. |
| 2002/0086216 | A1 | 7/2002 | Sekino et al. |
| 2003/0143465 | A1 | 7/2003 | Takahashi et al. |

FOREIGN PATENT DOCUMENTS

| | | | |
|---|---|---|---|
| JP | 01-006384 | A2 | 1/1989 |
| JP | 01-014881 | A2 | 1/1989 |
| JP | 64-002258 | A2 | 1/1989 |
| JP | 02-174070 | A2 | 7/1990 |
| JP | 03-192663 | A2 | 8/1991 |
| JP | 05-047369 | A2 | 2/1993 |
| JP | 05-047384 | A2 | 2/1993 |
| JP | 05-074462 | A2 | 3/1993 |
| JP | 05-151995 | A2 | 6/1993 |
| JP | 05-174872 | A2 | 7/1993 |
| JP | 05-325968 | A2 | 12/1993 |
| JP | 06-203829 | A2 | 7/1994 |
| JP | 06-349493 | A2 | 12/1994 |
| JP | 07-335263 | A2 | 12/1995 |
| JP | 08-022841 | A2 | 1/1996 |
| JP | 08-185851 | A2 | 7/1996 |
| JP | 08-222272 | A2 | 8/1996 |
| JP | 11-288704 | A2 | 10/1999 |
| JP | 2000260475 | A2 | 9/2000 |
| JP | WO 01/82398 | A1 | 11/2001 |
| WO | WO 00/50925 | A1 | 10/1999 |

OTHER PUBLICATIONS

D. Linden, Handbook of Batteries, $2^{nd}$ Ed., Copyright 1995 by McGraw-Hill, Inc. New York, pp. 36.4-36.17 (See especially Fig. 36.2).

P. Dan et al., More Details on the New $LiMnO_2$ Rechargeable Battery Technology Developed at Tadiran, Journal of Power Sources, 1997, pp. 443-447, vol. 68.

M. Broussely et al., Lithium Insertion Into Host Materials: The Key To Success For Li Ion Batteries, Electrochimica Acta, 1999, pp. 3-22, vol. 45 (See generally; esp. Fig. 1).

H. Tsukamoto, Synthesis and Electrochemical Studies of lithium transition metal oxides for lithium-ion batteries, Department of Chemistry, University of Aberdeen, 1999 (See table 1; Fig. 1-6).

Y. Lee et al., Synthesis and Electrochemical Characterization of Orthorhombic $LiMnO_2$ Material, Department of Applied Chemistry, Saga University, honjo 1, Saga 840-8502, Japan (1 page).

P. Meadows et al., Implantable Pulse Generators Using Rechargeable Zero-Volt Technology Lithium-Ion Batteries, U.S. Appl. No. 09/627,803, filed with USPTO Jul. 28, 2000, 54 pp.

International Search Report, dated Aug. 27, 2001, received in relation to Application No. PCT/US01/13308.

PCT Patent Application as filed on Nov. 19, 2001, in Application No. PCT/US01/43820.

* cited by examiner

| | Positive Active Material | Negative Substrate Material | Temperature | Result |
|---|---|---|---|---|
| (1) | $LiCoO_2$ | Copper | 25 °C | Fail; 79.9% Retention |
| | | | 37 °C | Fail; 76.2% Retention |
| (2) | $LiCoO_2$ | Titanium | 25 °C | Pass; 98.6% Retention |
| | | | 37 °C | Fail; 73.5% Retention |
| (3) | $LiNi_{0.8}Co_{0.2}O_2$ | Copper | 25 °C | --- |
| | | | 37 °C | Fail; 90% Retention |
| (4) | $LiNi_{0.8}Co_{0.2}O_2$ | Titanium | 25 °C | --- |
| | | | 37 °C | Pass; 98.8% Retention |

Figure 5.

RECHARGEABLE LITHIUM BATTERY FOR TOLERATING DISCHARGE TO ZERO VOLTS

CROSS-REFERENCE TO RELATED APPLICATIONS

This application is a Continuation-in-Part of PCT Application PCT/US01/43820 filed Nov. 19, 2001; and a Continuation-in-Part of U.S. application Ser. No. 09/675,287 filed Sep. 29, 2000 now U.S. Pat. No. 6,596,439; and a Continuation-in-Part of U.S. application Ser. No. 10/217,967 filed Aug. 13, 2002, which is a Divisional of U.S. application Ser. No. 09/675,287 filed Sep. 29, 2000 now U.S. Pat. No. 6,596,439, which claims the benefit of U.S. Provisional Application 60/199,895 filed Apr. 26, 2000.

STATEMENT REGARDING FEDERALLY SPONSORED RESEARCH OR DEVELOPMENT

No Applicable

REFERENCE TO A "SEQUENCE LISTING"

Not Applicable

BACKGROUND OF THE INVENTION

1. Technical Field

This invention relates generally to rechargeable electric batteries particularly suited for applications, e.g., implanted medical devices, where a battery cannot be easily replaced. More particularly, the invention relates to rechargeable lithium batteries configured to tolerate deep discharging to zero volts without permanently damaging the battery's energy storing capability.

2. Background Art

Rechargeable electric batteries are employed in a wide range of applications, e.g., consumer products, medical devices, and aerospace/military systems, which respectively impose different performance requirements. In some applications, e.g., implanted medical devices, it is important that the battery be able to reliably maintain its performance characteristics over a long useful life despite extended periods of inactivity. Implanted medical device applications impose special requirements on a battery because the medical device needs to be highly reliable to perform critical tasks, the battery may remain inactive and uncharged for extended periods, e.g., several months, and it is difficult and/or expensive to replace a battery. Analogous conditions exist in various aerospace/military applications. For example, a rechargeable battery may be deployed to power a satellite in deep space where it cannot be replaced and must be able to operate over a long life under varying conditions, including long periods of inactivity. Military applications often demand similar performance specifications since military hardware can be unused for several months but must remain ready to be activated. Current battery technology requires stored batteries to be charged every few months to avoid a permanent reduction in energy storing capability.

In order to avoid unnecessary surgery to replace a damaged battery in an implanted medical device, it is desirable that a battery perform reliably over a very long life, i.e., several years, under a variety of conditions. Such conditions can include extended periods of non-use which may allow the battery to deeply self discharge to zero volts. It is typical for prior art rechargeable lithium batteries to suffer a permanent capacity loss after discharging below 2.5 volts. To avoid such capacity loss, it is important to regularly charge prior art lithium batteries.

Existing rechargeable lithium batteries typically consist of a case containing a positive electrode and a negative electrode spaced by a separator, an electrolyte, and feedthrough pins respectively connected to the electrodes and extending externally of the case. Each electrode is typically formed of a metal substrate that is coated with a mixture of an active material, a binder, a solvent, and sometimes a conductor. In a typical battery design, the electrodes comprise sheets which are rolled together, separated by separator sheets, and then placed in a prismatic or cylindrical case. Positive and/or negative feedthrough pins (i.e., terminals) are then connected to the respective electrodes and the case is filled with electrolyte and then sealed. The negative electrode is typically formed of a copper substrate carrying graphite as the active material. The positive electrode is typically formed of an aluminum substrate carrying lithium cobalt dioxide as the active material. The electrolyte is most commonly a 1:1 mixture of EC:DEC in a 1.0 M salt of $LiPF_6$. The separator is frequently a microporous membrane made of a polyolefin, such as a combination of polyethylene and/or polypropylene which can, for example, be approximately 25 microns thick.

Batteries used in implanted medical devices can be charged from an external power source utilizing a primary coil to transfer power through a patient's skin to a secondary coil associated with the implanted medical device. The secondary coil and an associated charging circuit provide a charging current to the battery. Protection circuitry is typically used in conjunction with prior art lithium batteries to avoid the potential deleterious effects of over charging or overdischarging the battery. Such protection circuitry can terminate charging if the voltage or temperature of the battery exceeds a certain level. Moreover, it is common to also incorporate low voltage protection to disconnect the battery from its load if the voltage of the battery falls below a certain lower level. This latter precaution is taken to prevent permanent damage to the battery that will likely occur if the voltage on an electrode exceeds a Damage Potential Threshold (DPT). For example, it is well known in the industry that discharging a lithium battery to below 2.5 volts and storing it for an extended period of time will likely result in a permanent loss of battery capacity. Despite incorporating low voltage cutoff protection to disconnect the battery from its load if the voltage falls below a certain threshold, typical prior art batteries will slowly self-discharge further causing the voltage of an electrode to exceed the Damage Potential Threshold.

BRIEF SUMMARY OF THE INVENTION

The present invention is directed to a rechargeable lithium ion battery particularly configured to permit it to discharge to a very low voltage, e.g. zero volts, without causing permanent damage to the battery. More particularly, a battery in accordance with the invention is configured to define a Zero Volt Crossing Potential (ZCP) which is lower than the battery's Damage Potential Threshold (DPT).

ZCP refers to the voltage on the positive and negative electrodes relative to a lithium reference (Li/Li+) when the battery potential, i.e., the voltage between the electrodes, is zero. The Damage Potential Threshold (DPT) is attributable to at least two factors, i.e., a Substrate Dissolution Potential (SDP) and a Film Dissolution Potential (FDP). SDP refers to the voltage of the negative electrode, relative to the lithium reference, above which the electrode substrate starts to corrode, dissolve, or decompose to permanently damage the substrate. FDP refers to the voltage of the negative electrode, relative to the lithium reference, above which a solid electrolyte interface (SEI) layer begins to dissolve or decompose. The SEI, or film, comprises a passivation layer which, in normal operation, forms on the negative electrode and functions to inhibit a continuing reaction between the negative electrode active material and the electrolyte. When the voltage of the negative electrode relative to the lithium reference, exceeds either SDP or FDP, physical damage to the electrode is likely to occur thereby permanently impairing the battery's capacity.

A battery's ZCP level relative to the lithium reference is dependent in part on the materials used for the positive and/or negative electrodes. In accordance with a preferred embodiment of the invention, a positive electrode active material $LiNi_xCo_{1-x}O_2$ is selected which exhibits a discharge voltage curve appropriate to achieve a relatively low Zero Crossing Potential (ZCP) level. This feature of the preferred embodiment facilitates the implementation of a battery characterized by a ZCP less than its Damage Potential Threshold (DPT). It has been recognized that as more Ni is substituted for Co (i.e., increasing x), the slope of the discharge potential curve becomes more negative. It has been determined that values of x between 0.5 and 1.0 optimally achieve the desired ZCP/DPT relationship in accordance with the present invention, i.e., $LiNi_xCo_{1-x}O_2$ (where $0.5 \leq x \leq 1.0$). For x<0.5, there is a noticeable degradation in capacity retention after storage at zero volts indicating that some corrosion or internal battery degradation has occurred at low voltage similar to the results seen from a conventional lithium battery design.

In accordance with a preferred embodiment of the invention, $LiNi_{0.8}Co_{0.2}O_2$ is used for the positive active material on a thin metal substrate, e.g., aluminum. The negative electrode is preferably formed of a titanium or titanium alloy substrate carrying a layer of negative active material, e.g., graphite coated on both faces of the substrate.

Batteries in accordance with the present invention are particularly suited for use in critical applications where physical access to the battery is difficult and/or expensive, such as in medical devices configured to be implanted in a patient's body. Such a medical device is typically comprised of a hermetically sealed housing formed of biocompatible material and dimensioned to be implanted without interfering with normal body function. A battery in accordance with the invention includes a case configured for mounting in the device housing. The battery case can be of a variety of shapes, e.g., prismatic or cylindrical, and typically defines a volume of between 0.05 cc and 30 cc. Batteries within this range exhibit capacities between 1.0 milliamp hours and 10 amp hours. An exemplary battery for use in a neurostimulation device includes a prismatic hermetically sealed battery casing having dimensions of 35 mm×17 mm×5.5 mm. A wide variety of medical device applications are discussed in the medical and patent literature; see, for example, U.S. Pat. No. 6,185,452.

BRIEF DESCRIPTION OF THE SEVERAL VIEWS OF THE DRAWINGS

The above and other features and uniqueness of the invention will be better visualized from the following drawings and schematics.

FIG. 5 is a table showing test results of various battery configurations including a preferred embodiment in accordance with the present invention;

DETAILED DESCRIPTION OF THE INVENTION

A rechargeable battery in accordance with the present invention is particularly suited for use in medical devices intended to be implanted in a patient's body. Such medical devices are extensively discussed in the medical and patent literature. For example, U.S. Pat. No. 6,185,452 describes a Battery-Powered Patient Implantable Device utilizing a rechargeable battery depicted in alternative constructions in FIGS. 8A through 8G. The present invention is directed to an improved rechargeable lithium battery, useful in devices of the type described in U.S. Pat. No. 6,185,452, configured to tolerate deep discharging without significantly impairing the battery's ability to recover its original storage capacity. The present invention is also useful in various aerospace/military applications. For example, a rechargeable battery may be deployed to power a satellite in deep space where it cannot be replaced and must be able to operate over a long life under varying conditions, including long periods of inactivity. Military applications often demand similar performance specifications since military hardware can be unused for several months but must remain ready to be activated. Current battery technology requires stored batteries to be charged every few months to avoid a permanent reduction in energy storing capacity.

Figure 1A:
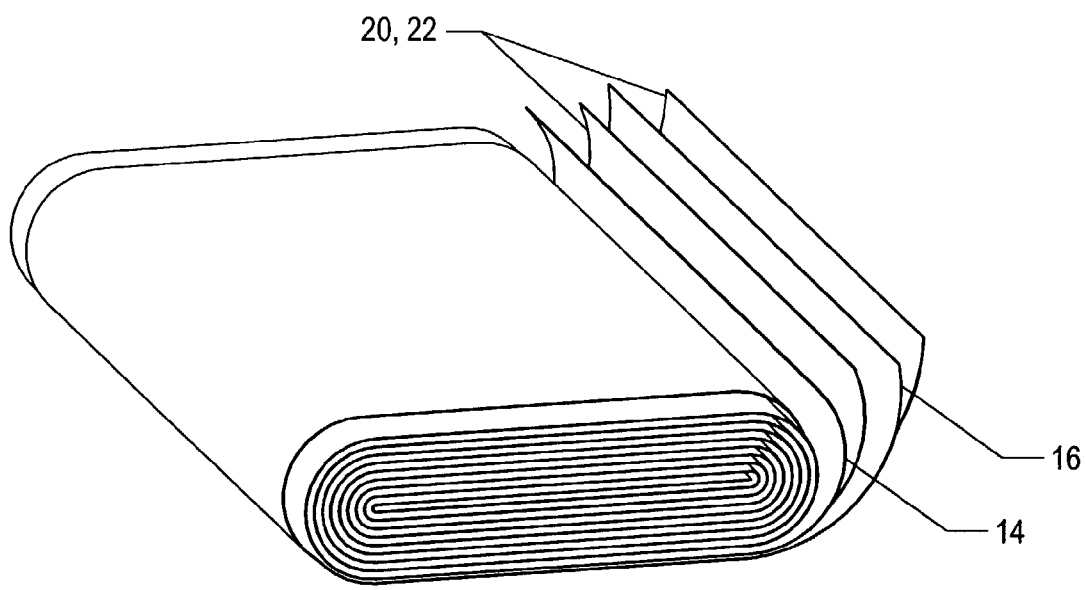
FIG. 1A schematically depicts positive and negative battery electrodes rolled around a mandrel for placement in a battery case and FIG. 1B depicts in cross-section a complete battery.
Figure 1B:
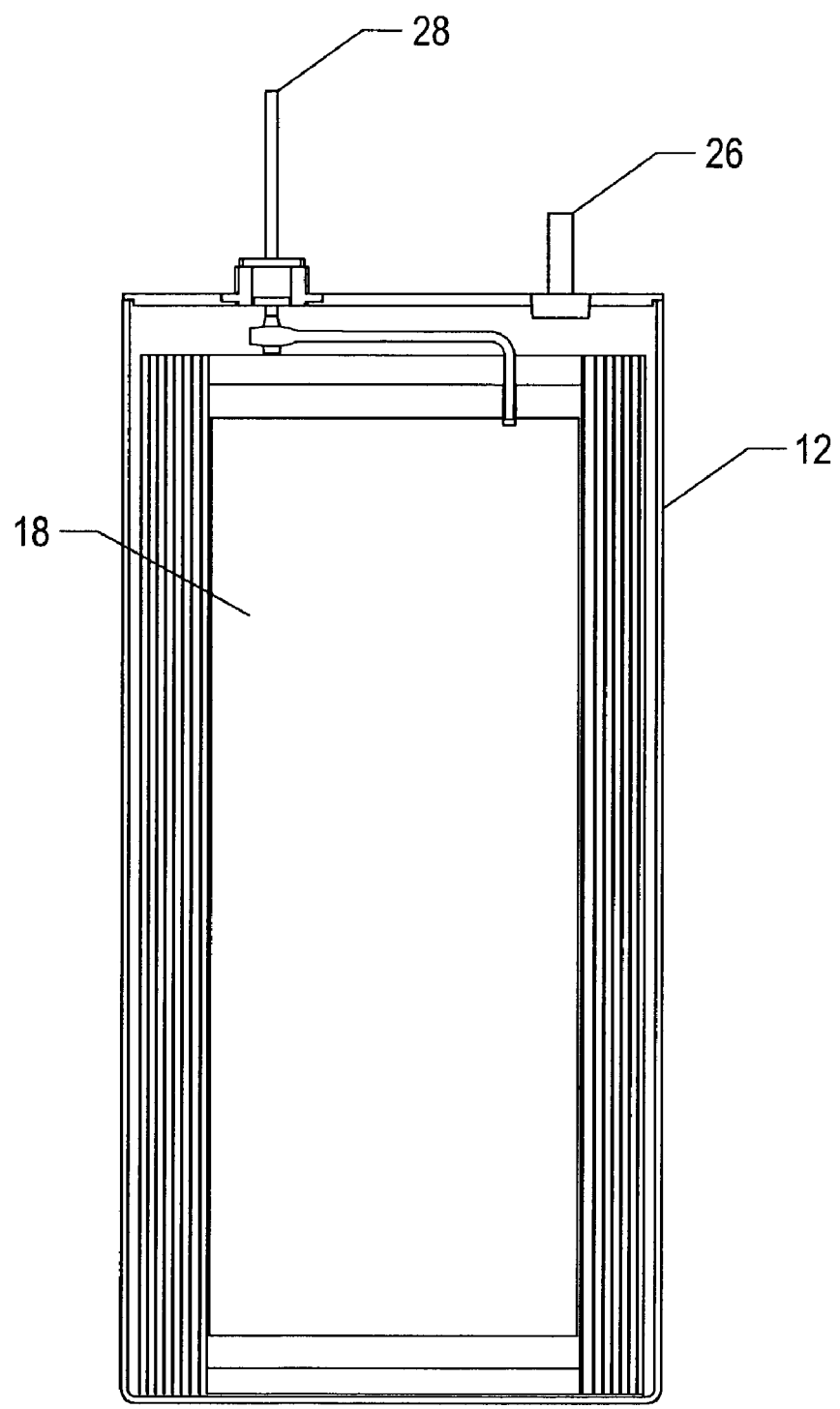

FIGS. 1A and 1B schematically depict a typical lithium battery construction 10 comprising a prismatic case 12 containing a positive electrode 14 and a negative electrode 16, rolled around a mandrel 18. Separator sheets 20, 22 are incorporated in the rolling to electrically separate the electrodes. The case 12 also typically includes electrolyte material (not shown) and positive and negative feedthrough pins (i.e., terminals) 26, 28 which are respectively connected to the electrodes 14, 16 and extend externally of the case 12.

Typical prior art lithium ion batteries include a positive electrode 14 comprising a thin metal substrate, e.g., aluminum, carrying a layer of positive active material, e.g., lithium cobalt dioxide $LiCoO_2$ mixed with a binder, and coated on both faces of the substrate. The negative electrode 16 typically comprises a thin metal substrate, e.g., copper, carrying a layer of negative active material, e.g., graphite coated on both faces of the substrate.

Two layers of separator 20, 22 electrically separate the electrodes 14, 16 from each other, enabling the electrodes to be rolled around mandrel 18. Each separator layer can comprise a microporous membrane made of a polyolefin, such as polypropylene or polyethylene, and is approximately 25 μm thick. The electrolyte is most commonly a 1:1 mixture of EC:DEC in a 1.0 M salt of $LiPF_6$.

Figure 2:
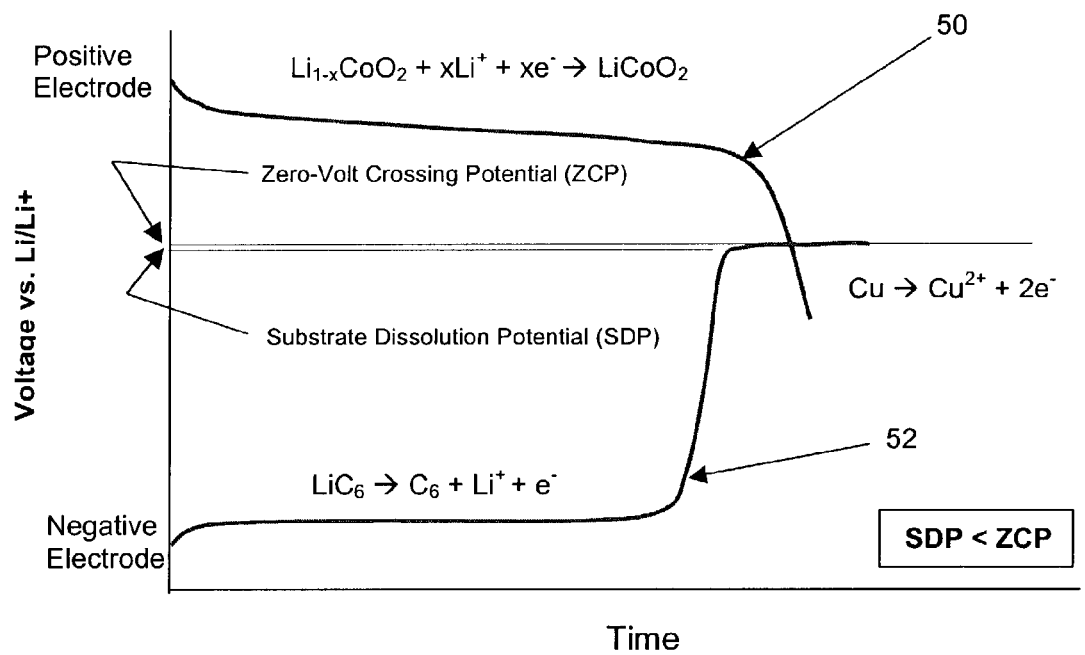
FIG. 2 shows a typical deep discharge curve for a conventional lithium ion battery using copper as the negative electrode substrate and lithium cobalt dioxide $LiCoO_2$ as the positive electrode active material.

FIG. 2 shows typical deep discharge performance curves for a conventional lithium ion battery. The y-axis represents voltage relative to a lithium reference (Li/Li+) or counter electrode and the x-axis represents time. Curves 50 and 52 respectively depict the discharge curves for the positive and negative electrodes. The battery output voltage is the difference between the positive electrode potential and the negative electrode potential. During discharge, the positive electrode potential decreases relative to the lithium reference and the negative electrode potential increases, primarily near the end of discharge. A protection or management circuit (not shown) is typically provided to disconnect the load to stop the discharge when the battery voltage reaches 2.5 volts. If, however, the discharge continues (attributable, for example, to self-discharge over a long period of time), the negative electrode potential will rise until it reaches the potential of the positive electrode. This constitutes the Zero Volt Crossing Potential (ZCP) and is typically about 3.6 volts in conventional lithium ion battery constructions. The negative electrode potential at ZCP can exceed the Substrate Dissolution Potential (SDP) of the negative electrode substrate, e.g., 3.3 volts for copper, and cause decomposition and permanent damage to the substrate.

Figure 3:
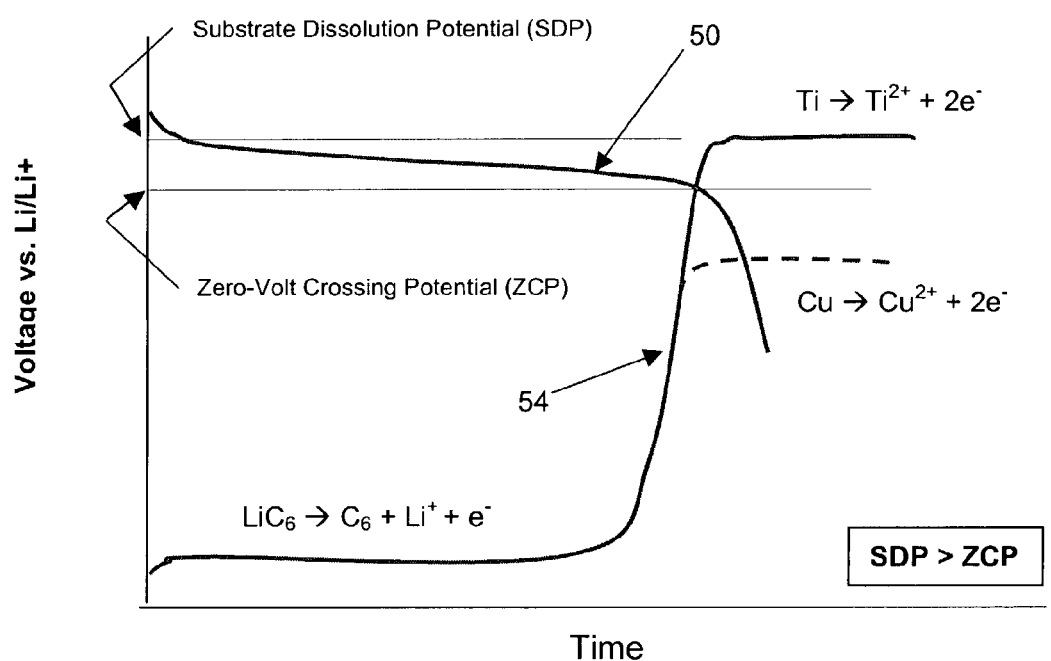
FIG. 3 shows a typical deep discharge curve for a lithium ion battery in accordance with the present invention using titanium as the negative electrode substrate.

The present invention is directed to battery improvements to assure that the value of SDP is greater than the value of ZCP, as represented in FIG. 3. The protection circuit is part of the load connected to the battery, and remains connected even after reaching the lower voltage limit. The overcharge (overvoltage) and overdischarge (undervoltage) protection functions are provided by the same circuit; therefore, even with a battery that is capable of being discharged to zero volts, the battery will likely still be provided with an overdischarge protection function.

FIG. 3 depicts deep discharge performance curves for a lithium battery in accordance with the present invention in which the negative electrode substrate is formed of titanium instead of copper. The use of titanium increases the knee of the negative electrode curve 54 to position the SDP level above the ZCP level. This relationship considerably reduces potential damage to the negative electrode substrate. In addition to commercially pure titanium, i.e., titanium CP, other materials can be used to raise the SDP sufficiently, e.g. titanium alloys, nickel, nickel alloys, and stainless steel. For both the positive and negative substrates, a thin sheet of foil is preferred to an expanded or perforated material. The thickness of the negative foil is preferably between 1 and 100 μm, more preferably between 5 and 30 μm, and most preferably between 5 and 20 μm. The thickness of the positive foil is preferably between 1 and 100 μm, more preferably between 5 and 40 μm, and most preferably between 10 and 40 μm.

FIG. 3 demonstrates how the SDP level can be increased relative to the ZCP by proper choice of the negative electrode substrate material. Alternatively, or additionally, the ZCP level can be decreased relative to the SDP by proper choice of the positive electrode active material, as depicted in FIG. 4.

As mentioned above, the ZCP in conventional lithium ion battery constructions is typically about 3.6 volts and the ZCP can exceed the SDP of the negative substrate, e.g., 3.3 volts for copper. FIGS. 2–4 show ZCPs that are close to or greater than the SDP of copper (3.3 V). Keeping ZCP above 3 V ensures that the positive electrode is not damaged and provides more energy since the positive potential remains higher than in prior art batteries throughout discharge.

Figure 4:
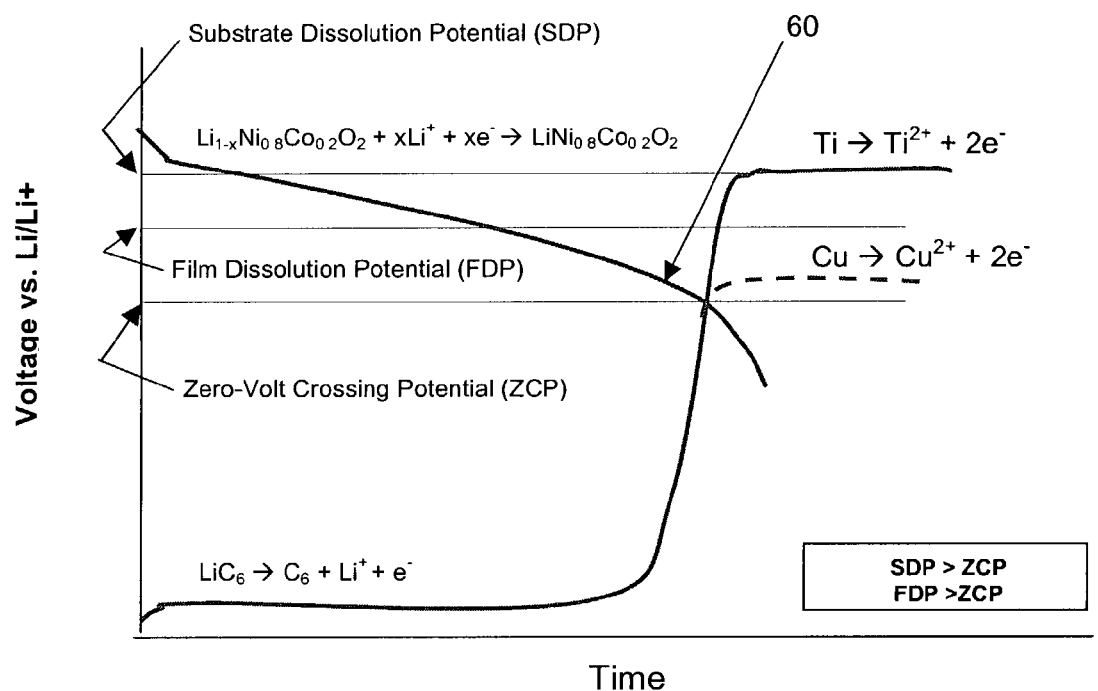
FIG. 4 shows a typical deep discharge curve for a lithium ion battery in accordance with the present invention using $LiNi_xCo_{1-x}O_2$ ($0.5 \leq x \leq 1.0$) as the positive electrode active material.

More particularly, FIG. 4 shows the discharge curve 60 for a positive electrode using lithium nickel cobalt dioxide $LiNi_xCo_{1-x}O_2$ (where $0.5 \leq x \leq 1.0$) as the active material, i.e., as the intercalation compound. Note that the curve 60 of FIG. 4 exhibits a greater negative slope than the analogous curve 50 of FIG. 2 representing the standard intercalation compound $LiCoO_2$. The effect of the increased negative slope is to lower the ZCP level relative to the lithium reference and the SDP level. As was the case in connection with FIG. 3, this reduces the potential damage to the negative electrode substrate. Additionally, however, the ZCP level also falls below a Film Dissolution Potential (FDP), which is the voltage above which a solid electrolyte interface (SEI) layer begins to dissolve. The SEI, or film, comprises a passivation layer which forms on the negative electrode and functions to inhibit a continuing reaction between the negative electrode active material and the electrolyte. Dissolution of the SEI can noticeably damage the negative electrode active material. When the SEI layer undergoes decomposition, it must be recreated. The act of recreating the SEI layer consumes lithium, irreversibly losing battery capacity in the process. In a preferred embodiment, the negative active material consists of carbon, which is relatively inexpensive, and is one of the negative active materials that forms an SEI layer.

Experiments have been performed at two different temperatures employing the aforedescribed techniques depicted in FIGS. 3 and 4. The preliminary results are summarized in the table of FIG. 5. Four different battery configurations were constructed as shown. Configuration (1) corresponds to the conventional arrangement represented in FIG. 2 comprising a copper substrate for the negative electrode and $LiCoO_2$ for the positive active material. The battery was built (including the step of battery formation) and then recycled once to get an initial capacity measurement. The battery was then shorted with a resistor between the positive and negative leads to achieve a zero volt state. This zero volt condition was held for one week and then recharged and discharged to get a capacity measurement after zero-volt storage. The capacity retention is calculated by dividing the discharge capacity after zero volt storage by the initial capacity and multiplying by 100%. In this manner, this percentage reflects any damage that had occurred to the battery while in the zero volt state.

As represented in FIG. 5, the capacity retention for battery configuration (1) is below 80%, thus suggesting that the zero volt condition had significantly damaged the battery. After opening the battery and examining the electrodes, it was seen that dissolution of the negative electrode copper substrate had occurred. This battery (1) configuration performed poorly at both temperature settings.

The battery configuration (2) used $LiCoO_2$ as the positive active material and a titanium substrate as the negative substrate corresponding to the arrangement represented in FIG. 3. The results show that at 25° C. the capacity retention was at about 98% after the zero volt condition. However, at a higher temperature (37° C.) exemplary of medical implant conditions, performance deteriorates to below 80%. This suggests that perhaps the zero volt crossing potential was sufficiently below SDP to avoid substrate dissolution but still high enough to exceed FDP and cause damage to the negative electrode active material. Accordingly, attempts were made to lower ZCP further to avoid damage both to the negative active material and the negative electrode substrate.

The battery configuration (3) utilizes $LiNi_xCo_{1-x}O_2$ (where x=0.8) as the positive electrode active material and a conventional copper negative electrode substrate. The results show that at 37° C., the capacity retention is quite high at 90%. However, examination after the test revealed that some dissolution of the copper substrate had occurred. Battery configuration (4) uses both $LiNi_{0.8}Co_{0.2}O_2$ as the positive active material and titanium as the negative electrode substrate material. Results show that this configuration gives the best capacity retention after zero volt storage.

From the curves of FIG. 4 and the table of FIG. 5, it appears that some performance gain is achieved by configuration (2) using a titanium negative electrode substrate and by configuration (3) using $LiNi_xCo_{1-x}O_2$ (where x=0.8) as the positive active material. However, maximum performance gain appears in configuration (4), which combines both of these features.

It should be noted that in order for the invention to be useful for allowing storage at zero volts, the relationship DPT>ZCP must be satisfied for the temperature at which the battery will be stored. FIG. 5 shows that the combination of Ti negative substrate with $LiCoO_2$ passed at 25° C. but failed at 37° C., and therefore, could not be stored at 37° C. without damage to the battery, manifested as loss of capacity.

When designing a battery, there are certain tradeoffs to be made. In addition to the ability to store a battery at zero volts, a battery having a high energy density, such as at least 100 Wh/l, is also desirable. $LiCoO_2$ has an energy density of about 150 mAh/g, while a $LiNiO_2$ has an energy density of about 220 mAh/g, and $LiNi_xCo_{1-x}O_2$ has an energy density between about 150 and 220 mAh/g. Another design goal is to have a high cycling capability. Prior art batteries typically have a life of 300 to 500 cycles. By contrast, the battery of the present invention has a life of about 500 to 4000 cycles. Furthermore, some prior art batteries may have diminished cycle life at higher temperatures, such as body temperature (37° C.). Thus, the operating temperature must be considered when choosing a battery chemistry. For example, some of the systems containing manganese are known to have worse cycle life at 50° C. These systems may also have lowered cycle life at body temperature.

Experimentally, a Ni content of x=0.5 was found to be thermally more stable than a Ni content of x=0 or 0.8 or 1. A Ni content of x=0.8 had a higher capacity and better high temperature (>35° C.) performance than $LiCoO_2$. Although a Ni content of x=1 has a large capacity, it was found to be thermally unstable and had low cycling capability. Therefore, considering factors together, such as zero volt storage capability, capacity, cycling capability, and thermal stability, we prefer a nickel content of about 0.8.

In addition to the examples of positive active materials given herein, other lithium transition metal oxides may be used in material combinations and conditions that produce the relationship that ZCP<DPT. Use of an oxide for the positive active material generally provides a higher positive potential, and therefore, higher battery voltage. Additives such as Ni, Co, Mn, Al, Mg, B, Ti, and Li in the amount of about 2% to about 5% may be included in the positive active material to strengthen crystal structure and/or improve thermal stability and/or increase capacity. Our preferred embodiment includes an aluminum additive. We have found that these additives in this amount do not significantly affect the discharge curves and do not affect the relationship between ZCP and DPT.

In a typical prior art battery, when the battery has discharged to a voltage of about 1 V, copper dissolution occurs. The battery is expected to discharge to below 1 V within about 8 to 12 months with a load, or about 3½ years with no load.

Figure 7:
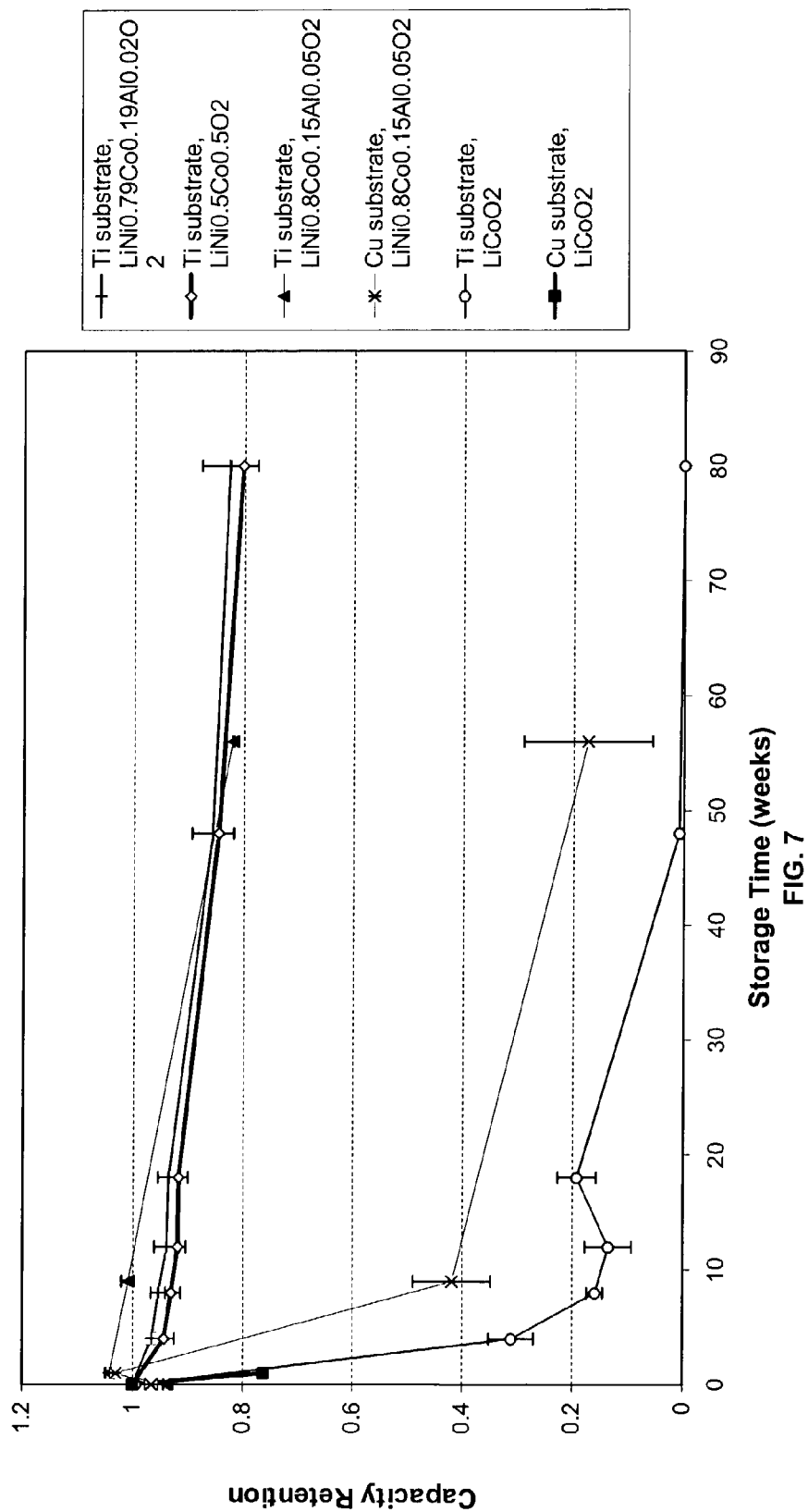
FIG. 7 shows capacity retention after long-term storage for various embodiments of the invention of the present invention as compared with a prior art battery.

In contrast, as shown in FIG. 7, batteries according to two embodiments of the present invention, using a titanium negative substrate with a lithium nickel cobalt oxide positive active material retained a capacity of about 80% after 80 weeks at a zero volt condition, and are expected to remain functional after 5 years storage at zero volts. Generally, for applications for which the battery is recharged only after an interval of six months or longer, we prefer a battery that retains at least 70% of its initial capacity after 1 year at 0 V. As can be seen in FIG. 7, the capacity of a battery of the present invention continues to diminish slightly during zero volt storage, but the rate at which the capacity diminishes appears to be decreasing. It is believed that some of the processes occurring to reduce capacity, particularly at the beginning, include initial thickening of the SEI layer, slight oxidation of the positive electrode, and electrolyte reduction or oxidation. For the battery of the present invention, after a period of zero volt storage, the SEI layer ceases to grow, the reactive impurities have been consumed, and therefore, the capacity stabilizes.

As can be seen from FIG. 4, the positive electrode has a maximum positive operating potential ($POP_{max}$) that is greater than SDP and/or FDP. The FDP is shown in FIG. 4 to be between the SDP of Ti and Cu, which is about 3.3 V, and the $POP_{max}$ is above FDP. Therefore, the $POP_{max}$ is greater than about 3.3 V in the examples of the preferred embodiment. It can be reasoned that if the $POP_{max}$ of the battery were below both the SDP and the FDP of the negative electrode, there would be no need to select materials and conditions to satisfy the relationships that SDP>ZCP and FDP>ZCP because the negative electrode cannot rise above the maximum positive operating potential and therefore could never reach a damaging potential. However, such a battery would typically have a battery voltage that is too low to be useful in many applications for which zero volt storage capability is desirable. For example, to power a chip in certain implantable devices requires a battery voltage greater than 2.7 V.

Specific properties are known to affect DPT, SDP, FDP, and ZCP. ZCP is a function of the negative substrate, temperature, and positive and negative active materials. DPT is a function of the positive active material, temperature, and film on the negative electrode. For example, as the temperature is increased, the film dissolution potential is decreased, thus reducing DPT.

The electrolyte may be a liquid, gel, or solid polymer, and the lithium salt dissolved therein is not limited to $LiPF_6$. For the test results shown in FIGS. 2–5, a 1.2-M solution of $LiPF_6$ in a 30:70 mixture of EC:DEC was used. We now prefer an EC content of about 5 to 50%, and more preferably about 19–30%. We also now prefer a solution having a lithium salt concentration of 0.8 to 1.8 M, with 1 to 1.5 M being more preferred. It is also preferred that the water content in the electrolyte be not more than 10 ppm with this electrolyte system. These preferences help keep the irreversible capacity lost on the formation of the SEI layer to an acceptable level without degrading other aspects of the battery. The SEI layer acts to form a thin passivation layer on the surface of the negative electrode and prevents further exfoliation of the graphite layers during lithium intercalation. If the EC content is too low, a stable protective SEI layer will not form on the negative electrode. This, in effect, reduces the capacity for the negative electrode to intercalate lithium. Obviously, the decrease in the capacity of the negative electrode greatly affects the charge-discharge performance and profiles during cycling. The cell will become what is called "negative limited" since the entire battery capacity is now limited by the capacity of the negative electrode that has degraded to a smaller capacity than the positive electrode.

In a preferred embodiment of the invention, the positive substrate is Al or SS, and the negative substrate is preferably Ti or SS. Ti is lighter than SS and therefore more desirable in certain applications. Preferably, the positive electrode active material comprises $LiNi_xCo_{1-x-y}M_yO_2$ wherein M is an element chosen from the group consisting of Mn, Al, Mg, B, Ti, and Li, and wherein $0.5 \leq x \leq 1$ and $0 \leq y \leq 0.3$ and more preferably, $0.6 \leq x$, $x \leq 1$, $0.02 \leq y$, and $y \leq 0.05$, and most preferably, $LiNi_{0.8}Co_{0.15}Al_{0.05}O_2$. Other ratios may be used, such as $LiNi_{0.79}Co_{0.19}Al_{0.02}O_2$.

Figure 6:
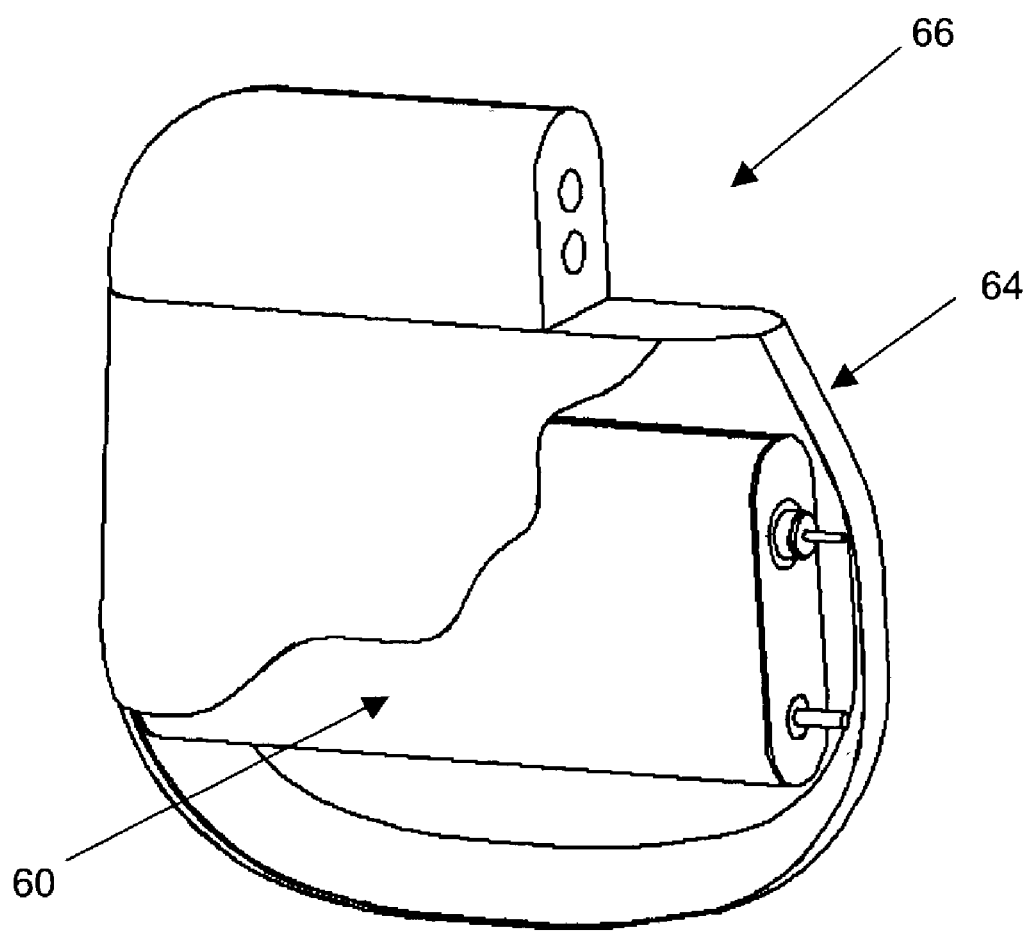
FIG. 6 schematically depicts a battery in accordance with the invention contained within an implantable medical device housing.

FIG. 6 schematically depicts a battery 60 in accordance with the invention mounted in a housing 64 (shown partially open for the purposes of illustration) of a medical device 66 configured for implanting in a patient's body. The housing 64 is preferably formed of biocompatible material and hermetically sealed. The device 66 is typically used for monitoring and/or affecting body parameters. For example, the device can be used to electrically stimulate nerves. The casing 68 of battery 64 can, for example, have dimensions of 35 mm×17 mm×5.5 mm. Other configurations and sizes are suggested in the literature, e.g., U.S. Pat. No. 6,185,452.

FIG. 7 shows capacity retention after long-term storage for various embodiments of the invention of the present invention as compared with batteries that are not able to retain high capacity after long-term storage. For each cell, a resistor was connected between the terminals to bring the battery voltage quickly to 0 V, and the cell was stored at 37° C. For each data point, the cells were cycled 5 times and the discharge capacities were measured and capacity retention calculated. As shown in the graph, those cells with copper substrates and/or positive active materials not comprising nickel lost more than 20% of their capacity in less than 10 weeks. In those cells having a titanium substrate and a positive active material $LiNi_xCo_{1-x-y}Al_yO_2$ comprising nickel in the amount x=0.5, 0.79, or 0.8, capacity retention was still greater than 80% after one year (52 weeks) at 37° C. zero volt storage.

Although a slightly different graphite composition was used for the negative active material in the two tests that used $LiNi_{0.8}Co_{0.15}Al_{0.05}O_2$ active material as compared to the other four tests, this difference is believed not to have affected the trend. In these two tests, at the first data point after time 0, the capacity appears to have increased slightly; it is speculated that battery formation had not yet been quite completed at time 0. The later data points are consistent with the trend that those cells with copper substrates lost more than 20% of their capacity in less than 10 weeks, and that those cells having titanium substrate and $LiNi_xCo_{1-x-y}Al_yO_2$ with $x \geq 0.5$ retained >80% of their initial capacity after one year.

A film dissolution potential (FDP) of a battery may be determined by using a working electrode comprising a substrate having an active material formed thereon, a lithium counter electrode, and a lithium reference electrode. The potential between the working and reference electrode is swept from its initial potential down to 0 volts versus Li to form the SEI layer on the active material, and then slowly increased while measuring current between the working and counterelectrode until the current density at the working electrode reaches a predetermined value. The potential at the working electrode when the current density reaches the predetermined value is the FDP. This predetermined value of the current density at the working electrode is preferably 1 $\mu A/cm^2$.

A damage potential threshold (DPT) of a battery may be determined using an electrochemical cell comprising a first working electrode comprising a substrate having an active material formed thereon, a lithium counter electrode, and a lithium reference electrode. The potential between the first working electrode and reference electrode is swept from its initial potential down to 0 volts versus Li to form an SEI layer on the negative active material; and then slowly increased while measuring current between the first working electrode and counterelectrode until the current density at the working electrode reaches a predetermined value. The potential at the first working electrode when the current density at the working electrode reaches the predetermined value is the FDP. A second working electrode comprising the substrate without active material is used to determine the substrate dissolution potential (SDP). The potential between the second working electrode and reference electrode is swept from its initial potential down to 0 volts versus Li; and then increased while measuring current between the second working and counterelectrode until the current density at the second working electrode is at least a predetermined value. The potential between the second working and reference electrode when current density at the second working electrode reaches the predetermined value is the SDP. The DPT is the lower of FDP and SDP. The predetermined value of the current density at the working electrode is preferably 1 $\mu A/cm^2$.

A method of implanting a battery into a patient comprises providing a battery comprising a positive electrode and a negative electrode, the positive electrode comprising a metal substrate having a first active material formed thereon and the negative electrode comprising a metal substrate having a second active material formed thereon, wherein the positive and negative electrodes define a ZCP relative to a reference level when the voltage between the electrodes is zero, and wherein the negative electrode is susceptible to permanent damage when a voltage exceeding a DPT is applied thereto, wherein the first active material and the negative electrode substrate material are selected to optimize a capacity retention of the battery by establishing the ZCP at a lower level than the DPT; and implanting the battery into a patient.

While some implanted medical devices such as cochlear implants, are generally needed on an ongoing basis, others, such as devices for pain mitigation, are needed only intermittently. When a device is implanted but then not needed for a period of time, the battery may be allowed to drain to very low voltage. In the event that the implanted device is again needed in the future, it is important that the battery still be capable of being recharged with a high battery capacity, close to its original capacity, without having to explant the battery and implant a new one. Even in those devices that are needed continuously, a patient may forget to recharge the battery, allowing the battery to drain to a very low level. Prior art batteries commonly contain protection circuitry to disconnect the battery from its load if the voltage of the battery (or any cell) falls below a certain lower level. However, these protection circuits are not 100% effective in preventing further discharge, both because it is not possible to completely disconnect the load and because of self discharge of the battery, each of which leads to a continuous current drain of about 0.1 μA to 10 μA. Under long-term storage conditions, the battery will eventually discharge to zero volts, damaging prior art batteries. Furthermore, the battery tends to discharge at a faster rate in the body than it would at room temperature.

Because of the ability of the battery of the present invention to withstand zero volt storage, the device may be implanted and then left in the body for six months, a year, or more before recharging, without adverse affect on the battery. A method for using a battery that is implanted into a patient comprises applying the battery to a load within the patient to cause discharging of the battery, wherein the battery comprises a positive electrode and a negative electrode, the positive electrode comprises a metal substrate having a first active material formed thereon and the negative electrode comprises a metal substrate having a second active material formed thereon, wherein the positive and negative electrodes define a ZCP relative to a reference level when the voltage between the electrodes is zero, and wherein the negative electrode is susceptible to permanent damage when a voltage exceeding a DPT is applied thereto; disconnecting the battery from the load once a potential difference between the positive and negative electrodes reaches a specified value, the value being greater than zero; allowing the battery to further discharge within the patient after disconnecting the battery from the load to a zero volt condition, wherein during discharge the DPT is maintained at a level higher than the ZCP; and recharging the battery after reaching the zero volt condition.

In addition to implanted medical devices that may not be recharged for six months or more, other applications require long-term storage capability, particularly in a harsh environment. For example, in aerospace applications, the battery may be subject to long-term storage and higher temperatures during launch, and there is a chance that a satellite battery may not be properly recharged, thus allowing it to discharge to a low voltage. In all of these cases, a battery may be provided that comprises a positive electrode and a negative electrode, the positive electrode comprising a metal substrate having a first active material formed thereon and the negative electrode comprising a metal substrate having a second active material formed thereon, wherein the positive and negative electrodes define a ZCP relative to a reference level when the voltage between the electrodes is zero, and wherein the negative electrode is susceptible to permanent damage when a voltage exceeding a DPT is applied thereto. This inventive battery may be used by applying the battery to a load to cause discharging of the battery such that the positive electrode potential decreases relative to the reference level and the negative electrode potential increases relative to the reference level, disconnecting the battery from the load when a potential between the positive and negative electrodes is greater than zero; allowing the battery to further discharge to below 1 V after disconnecting the battery from the load, wherein during discharge the DPT is maintained at a level higher than the ZCP; and recharging the battery after reaching 1 V. The battery may be maintained at less than 1 V for 3 days, 6 months, a year, or more, without destruction of the battery. When the battery is eventually recharged, it is preferably recharged to a discharge capacity of $\geq 70\%$ of its initial discharge capacity.

More generally speaking, the battery of the present invention may be used as follows: at a time $t_1$, providing a rechargeable battery having an initial discharge capacity; at a time $t_2$, charging the battery to a battery voltage of greater than 2.5 V; at a time $t_3$, allowing the battery to discharge to less than 1 V; and at a time $t_4$, recharging the battery to a discharge capacity of at least 70% of the initial discharge capacity after reaching a battery voltage of less than 1 V, wherein $t_4-t_2$ is at least 6 months.

While the invention has been described with reference to specific exemplary embodiments and applications, it should be recognized that numerous modifications and variations will occur to those skilled in the art without departing from the spirit and scope of the invention set forth in the appended claims. Furthermore, the features described for one embodiment may be combined with other embodiments disclosed herein.

What is claimed is:

1. A rechargeable lithium ion battery, comprising:
   a positive electrode having a first active material on a substrate, the first active material including $LiNi_xCo_{1-x-y}M_yO_2$ wherein M is an element chosen from the group consisting of Mn, Al, Mg, B, Ti, and Li, and wherein $0.5 \leq x \leq 1$ and $0 < y \leq 0.3$;
   a negative electrode having second active material on a substrate, the second active material including carbon;
   an electrolyte that reacts with the negative electrode to form a solid electrolyte interface (SEI) layer, the SEI layer being susceptible to damage when a voltage potential exceeding a Film Dissolution Potential (FDP) is applied thereto, and wherein the FDP is lower than the maximum positive operating potential of the battery;
   the positive electrode and the negative electrode defining a Zero Volt Crossing Potential (ZCP) relative to a reference level when the voltage between the positive electrode and the negative electrode is zero; and
   the electrolyte, the positive electrode and the negative electrode being configured such that the ZCP is lower than the FDP during storage at a predetermined temperature.

2. The battery of claim 1, wherein said negative electrode substrate is susceptible of permanent damage when a potential exceeding a Substrate Dissolution Potential (SDP) is applied thereto; and wherein
   the positive and negative electrodes are selected and configured to establish ZCP at a lower level than SDP in order to prevent dissolution of the negative substrate during storage at the predetermined temperature.

3. The battery of claim 1, wherein $x \geq 0.6$.

4. The battery of claim 1, wherein $x \leq 0.8$.

5. The battery of claim 1, wherein $y \leq 0.05$.

6. The battery of claim 1, wherein $y \geq 0.02$.

7. The battery of claim 1, wherein said negative electrode substrate is formed of a material selected from the group consisting of titanium and titanium alloy.

8. The battery of claim 1, wherein the negative electrode substrate is formed of stainless steel.

9. The battery of claim 1, wherein the negative electrode active material consists of carbon.

10. The battery of claim 1, wherein the electrolyte consists of a liquid electrolyte.

11. The battery of claim 10, wherein the liquid electrolyte comprises a lithium salt dissolved in EC:DEC.

12. The battery of claim 11, wherein the lithium salt is $LiPF_6$.

13. The battery of claim 1, wherein the predetermined temperature is body temperature.

14. The battery of claim 1, wherein the predetermined temperature is about 37° C.

15. The battery of claim 1, wherein the predetermined temperature is about 25° C.

16. The battery of claim 1, further comprising:
a battery management circuit that attempts to stop battery discharge when the battery voltage reaches 2.5 V, wherein the maximum battery voltage is greater than 2.5 V.

17. The battery of claim 1, wherein the ZCP is greater than about 3 V vs. Li/Li$^+$.

18. The battery of claim 1, wherein the positive electrode has a positive discharge curve having a negative slope over most of the positive discharge curve, wherein the negative slope is more negative than the negative slope over most of the discharge curve of $LiCoO_2$.

19. The battery of claim 1, further including a case for housing the positive and negative electrodes; and wherein the case is configured for implanting in a patient's body.

20. The battery of claim 19, wherein the case is hermetically sealed.

21. The battery of claim 1, wherein the element includes Mg.

22. The battery of claim 1, wherein the element includes B.

23. The battery of claim 1, wherein the element includes Ti.

24. The battery of claim 1, wherein the element includes Li.

* * * * *